United States Patent [19]

Harrington et al.

[11] Patent Number: 4,917,083

[45] Date of Patent: Apr. 17, 1990

[54] DELIVERY ARRANGEMENT FOR A LASER MEDICAL SYSTEM

[75] Inventors: James A. Harrington, Westlake Village, Calif.; Michael G. Clancy, Westford, Mass.

[73] Assignee: Heraeus Lasersonics, Inc., Santa Clara, Calif.

[21] Appl. No.: 164,236

[22] Filed: Mar. 4, 1988

[51] Int. Cl.[4] .............................................. A61B 17/36
[52] U.S. Cl. .................................... 606/15; 606/16; 606/19
[58] Field of Search ...................... 128/303.1, 395–398; 350/96.32; 372/64

[56] References Cited

U.S. PATENT DOCUMENTS

| | | | |
|---|---|---|---|
| 3,311,747 | 3/1967 | Smith et al. | 250/83.3 |
| 3,382,343 | 5/1968 | Muncheryan | 219/121 |
| 3,383,491 | 5/1968 | Muncheryan | 219/121 |
| 3,386,043 | 5/1968 | Mercatili et al. | 330/4.3 |
| 3,417,746 | 12/1968 | Moore et al. | 128/6 |
| 3,467,098 | 9/1969 | Ayres | 128/303.1 |
| 3,528,424 | 9/1970 | Ayres | 128/303.1 |
| 3,622,743 | 11/1971 | Munchervan | 219/121 LA |
| 3,821,510 | 6/1974 | Muncheryan | 128/303.1 |
| 3,834,391 | 9/1974 | Block | 128/303.1 |
| 3,902,036 | 8/1975 | Zaleckas | 219/121 L |
| 3,913,582 | 10/1975 | Sharon | 128/303.1 |
| 3,963,327 | 6/1976 | Poirier | 350/287 |
| 4,069,823 | 1/1978 | Isakov et al. | 128/303.1 |
| 4,122,853 | 10/1978 | Smith | 128/303.1 |
| 4,128,753 | 12/1978 | Sharp | 219/121 L |
| 4,161,944 | 7/1979 | Muckerheide | 128/654 |
| 4,170,997 | 10/1979 | Pinnow et al. | 128/395 |
| 4,207,874 | 6/1980 | Choy | 128/6 |
| 4,211,468 | 7/1980 | Steensma | 350/96.10 |
| 4,266,548 | 5/1981 | Davi | 128/303.1 |
| 4,398,790 | 8/1983 | Righini et al. | 350/96.18 |
| 4,423,726 | 1/1984 | Imagawa et al. | 128/303.1 |
| 4,429,211 | 1/1984 | Carstens et al. | 219/121 LC |
| 4,473,074 | 9/1984 | Vassiliadis | 128/303.1 |
| 4,475,788 | 10/1984 | Tomassini et al. | 350/96.20 |
| 4,483,585 | 11/1984 | Takami | 350/96.24 |
| 4,521,070 | 6/1985 | Sottini et al. | 350/96.15 |
| 4,532,400 | 7/1985 | Toida et al. | 219/121 LS |
| 4,533,814 | 8/1985 | Ward | 219/121 LD |
| 4,534,811 | 8/1985 | Ainslie et al. | 156/73.1 |
| 4,550,240 | 10/1985 | Toida et al. | 219/121 LS |
| 4,564,736 | 1/1986 | Jones et al. | 219/121 L |
| 4,574,180 | 5/1986 | Kasner et al. | 219/121 LY |
| 4,583,526 | 4/1986 | Ali | 128/6 |
| 4,583,539 | 4/1986 | Karlin et al. | 128/303.1 |
| 4,589,729 | 5/1986 | Bridges et al. | 350/96.32 |
| 4,597,380 | 7/1986 | Raif et al. | 128/6 |
| 4,618,759 | 10/1986 | Muller et al. | 219/121 LR |
| 4,626,649 | 12/1986 | Dupeyrat et al. | 219/121 LU |
| 4,641,912 | 2/1987 | Goldenberg | 350/96.10 |
| 4,658,817 | 4/1987 | Hardy | 128/303.1 |
| 4,659,916 | 4/1987 | Müller et al. | 250/201 |
| 4,671,273 | 7/1987 | Lindsey | 128/303.1 |
| 4,693,244 | 9/1987 | Daikuzono | 128/303.1 |
| 4,695,697 | 9/1987 | Kosa | 219/121 LZ |
| 4,696,062 | 9/1987 | LaBudde | 455/612 |
| 4,698,479 | 10/1987 | Rando et al. | 219/121 LV |
| 4,707,596 | 11/1987 | Hohberg | 250/201 |
| 4,713,825 | 12/1987 | Adsett | 372/64 |
| 4,714,815 | 12/1987 | Swarts et al. | 219/121 LC |
| 4,720,163 | 1/1988 | Goodwin et al. | 350/96.20 |
| 4,732,448 | 3/1988 | Goldenberg | 350/96.18 |
| 4,805,987 | 2/1989 | Laakmann et al. | 350/96.32 |

OTHER PUBLICATIONS

Baggish et al., "A Flexible $CO_2$ Laser Fiber for Operative Laparoscopy", *Fertility & Sterility*, Jul. 1986, pp. 16–20.

James A. Harrington, "Medical Needs Drive IR Fiber Development", *Photonics Spectra*, Jul. 1987, pp. 61–63.

Jenkins & Devereux, "Dispersion Phenomena in Hollow Alumina Waveguides" *IEEE Journal of Quantum Electronics*, vol. QE21, #10, 10/85, pp. 1722–1727.

*Primary Examiner*—Max Hindenburg
*Attorney, Agent, or Firm*—Flehr, Hohbach, Test, Albritton & Herbert

[57] ABSTRACT

A delivery arrangement for $CO_2$ (carbon dioxide) laser radiation is described which is particularly designed for laser medical systems. The delivery arrangement has three components—an articulated arm connectable to a $CO_2$ laser head, a waveguide probe for directing $CO_2$ laser radiation to an operating site, and a coupler for conditioning $CO_2$ laser radiation emanating from the arm for coupling into the waveguide probe.

9 Claims, 4 Drawing Sheets

DELIVERY ARRANGEMENT FOR A LASER MEDICAL SYSTEM

BACKGROUND OF THE INVENTION

The present invention relates to laser medical systems and, more particularly, to a medical radiation delivery arrangement which provides both desired flexibility and desired precision.

The output radiation of lasers now is widely used for treating various human and animal conditions. The nature of the delivery arrangement for the output laser radiation depends largely on the type of radiation to be delivered and the type of medical treatment or diagnostics. $CO_2$ (carbon dioxide) laser radiation is used both internally and externally of a human body to create incisions. The principal component of $CO_2$ radiation, e.g., 10.6 microns in wavelength, is in the infrared (IR) region of the electromagnetic spectrum and interacts favorably with tissue for surgery. However, methods and means which have been used in the past to deliver $CO_2$ radiation to an operating site are not ideal. The conventional delivery means is via an articulated arm. An articulated arm basically is an arrangement of tubing, corner reflectors (mirrors) and movable joints. Such an arm generally is from one to one and one-half meters in length and has up to seven mirrors. The arm terminates at its output end in a handpiece or a micromanipulator. A handpiece often is used when the treatment site is external to the body, and is a simple lens for focusing the output energy to a small spot directly at the treatment site. A micromanipulator typically includes a joystick to aim the radiation through an endoscope to a treatment site at its remote end. (An endoscope, as used generically here, is basically a hollow tube to be inserted into a body cavity.) The use of a handpiece or a micromanipulator-endoscope, places the last position at which the beam is manipulated a significant distance away from the operating site. In a sense, this is like shining a light to a desired position at a far end of a pipe. That is, there is no guiding of the radiation—the surgeon must physically manipulate the beam at a distance to achieve the desired action at an operating site.

An articulated arm is sturdy and provides desired flexibility for delivering $CO_2$ laser radiation. Because of its joints, such an arm enables a physician easily to vary the location to which output radiation is directed. This is a particularly important advantage during surgery. However, as discussed above, while an articulated arm provides desired flexibility, use of the same has not, until now, enabled the precise positioning that is necessary or desirable in many delicate operations.

Because of the problems mentioned above with articulated arms, some in the art have used optical waveguides, including fiberoptic and hollow air core waveguides, for the delivery of $CO_2$ laser radiation for surgery or other medical treatment or diagnostic purposes. While guides of this nature generally are fragile and/or rigid, they do provide a precise and constant relationship between an output radiation beam guided to their output ends and the physical location of such output ends. Use of the same by surgeons has therefore been made to obtain the precision of delivery of radiation to a tissue site which is often needed. When optical waveguides are used, though; much of the flexibility associated with articulated arms is sacrificed. Hollow waveguides generally either are rigid or have very restricted bend radii. While the hollow waveguide described in the paper entitled "A Flexible $CO_2$ Laser Fiber for Operative Laparoscopy" by Baggish, et al., published in the July 1986 issue of *Fertility and Sterility* is stated to be "flexible," it is a dielectrically coated metal (aluminum) tube having a restricted bend capability.

It should be noted that the desired flexibility cannot be regained simply by using an optical waveguide with a universally or articulated mounted laser. This does not provide the flexibility at the tissue site which is needed. When the waveguide is a fiberoptic probe, flexing can result in internal breakage and corresponding attenuation of the output. Moreover, the length of infrared fiberoptic guides, the type of waveguide applicable for transmitting $CO_2$ radiation, has been limited because of high infrared losses. The paper entitled "Medical Needs Drive IR Fiber Development" by one of the inventors hereof, James A. Harrington, appearing in the July 1987 issue of *Photonics Spectra* describes the various types of IR fibers and their limitations.

SUMMARY OF THE INVENTION

The present invention is a treatment radiation delivery arrangement for a laser medical system which retains the flexibility of an articulated arm while providing the precision associated with an optical waveguide. The arrangement is particularly useful when the treatment radiation to be delivered is $CO_2$ laser radiation. Broadly speaking, the invention includes the combination of three parts—an articulated arm, an optical waveguide, and a coupler positioned to receive medical radiation emanating from the output end of the articulated arm and condition the same for receipt at the entry end of the optical waveguide. In this connection, an optical waveguide generally will only guide radiation that it receives at its entry end if the radiation satisfies certain criteria. The angular relationship between radiation of an appropriate frequency and the direction of guiding at the entry end of a waveguide is defined by the "numerical aperture" of the guide. For example, the numerical aperture of a polycrystalline, metal halide fiber is about 0.46, whereas a tubular, hollow air core is approximately 0.03.

The coupler is an important aspect of the combination in assuring efficient coupling of energy from the articulated arm output end into the optical waveguide. It enables the desired accurate delivery to be provided without the need for alignment aids. As will be discussed below, a coupler is particularly important when the waveguide is a hollow air core guide since, among other reasons, such a waveguide has a very small numerical aperture.

The invention includes many other features which will be described or will become apparent from the following, more detailed description.

BRIEF DESCRIPTION OF THE DRAWINGS

With reference to the accompanying four sheets of drawings.

DETAILED DESCRIPTION OF PREFERRED EMBODIMENTS

Figure 1:
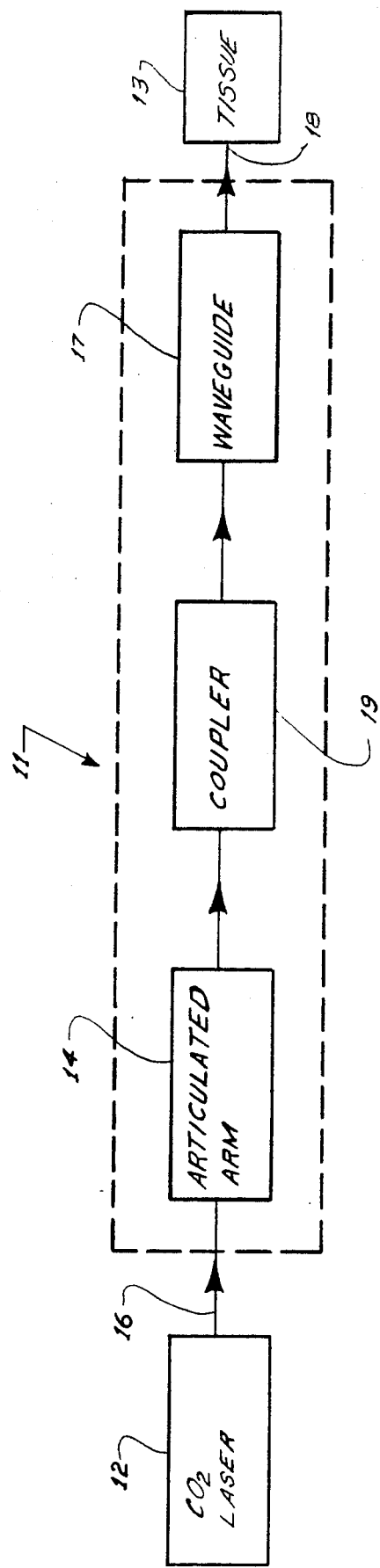
FIG. 1 is a block diagram illustrating a delivery arrangement of the invention delivering $CO_2$ laser radiation to a tissue treatment site.

With reference to FIG. 1, a coupling arrangement of the instant invention, generally indicated by the reference numeral 11, is illustrated schematically directing the output radiation of a $CO_2$ laser 12 to mammalian tissue 13 for a medical treatment purpose, e.g., to surgically create an incision within a human body.

As mentioned previously, in many situations the delivery arrangement for $CO_2$ laser radiation must be quite flexible, i.e., the surgeon or other treating physician must be able to direct the radiation output to a particular site without any significant resistance being imparted by the delivery arrangement itself. Articulated arms are used commonly for this purpose. Commercial construction of the same has evolved to the point at which a surgeon can obtain the desired flexibility without resistance. However, they are not sufficiently flexible or small enough to be used endoscopically (in the body). This has resulted in the use of micromanipulators-endoscopes on the ends of arms. The result has been a loss of the positioning accuracy associated with articulated arms. That is, in such arrangements, as well as in ones using handpieces on the ends of arms, the last location at which the direction of the beam is manipulated generally is a significant distance from the desired delivery site. As also mentioned previously, for this and other reasons in many situations surgeons and treating physicians have turned to optical waveguides to deliver $CO_2$ radiation. The problem with optical waveguides now available, though, is that they are either rigid or fragile.

The delivery arrangement of the instant invention combines the flexibility of an articulated arm with the precision of delivery associated with an optical waveguide, i.e., a device which transmits radiation by guiding its path. To this end, the delivery arrangement of the invention includes, in combination, an articulated arm 14 coupled, as is represented at 16, to a $CO_2$ laser to receive medical radiation therefrom and direct the same via articulations to its output end. An optical waveguide 17, such as a fiberoptic waveguide or a tubular, hollow air core waveguide, guides the radiation from the guide entry end to an exit end adjacent to an operating site 18 on the tissue 13. (As used herein, an "optical waveguide" is a device which transfers, with minimum energy loss, radiation having a wavelength in the ultraviolet, visible and/or infrared range from one end of the device to the other.) It must be kept in mind that an optical waveguide is not a conventional endoscope. That is, it is a device for guiding, with minimal loss, electromagnetic radiation in the optical region of the spectrum from an entry end to the distal or tissue end of the guide, whereas an endoscope simply is a pipe that provides little, if any, guiding of its own.

An optical coupler 19 is also included as part of the delivery combination to receive the radiation emanating from the articulated arm and condition the same for receipt at the entry end of the waveguide 17. In this connection, the entry ends of waveguides have numerical apertures which define the angular relationship that radiation must have in order to be coupled to the same. The coupler must focus the radiation to such end. Some optical waveguides, such as fiberoptic waveguides, also require that radiation received at the entry end not be sufficiently concentrated to cause burning or other deleterious effects at the same. Thus, the coupler of the invention is positioned and constructed to provide the conditioning to the radiation received from the articulated arm that may be required by the particular waveguide that is selected.

Figure 2:
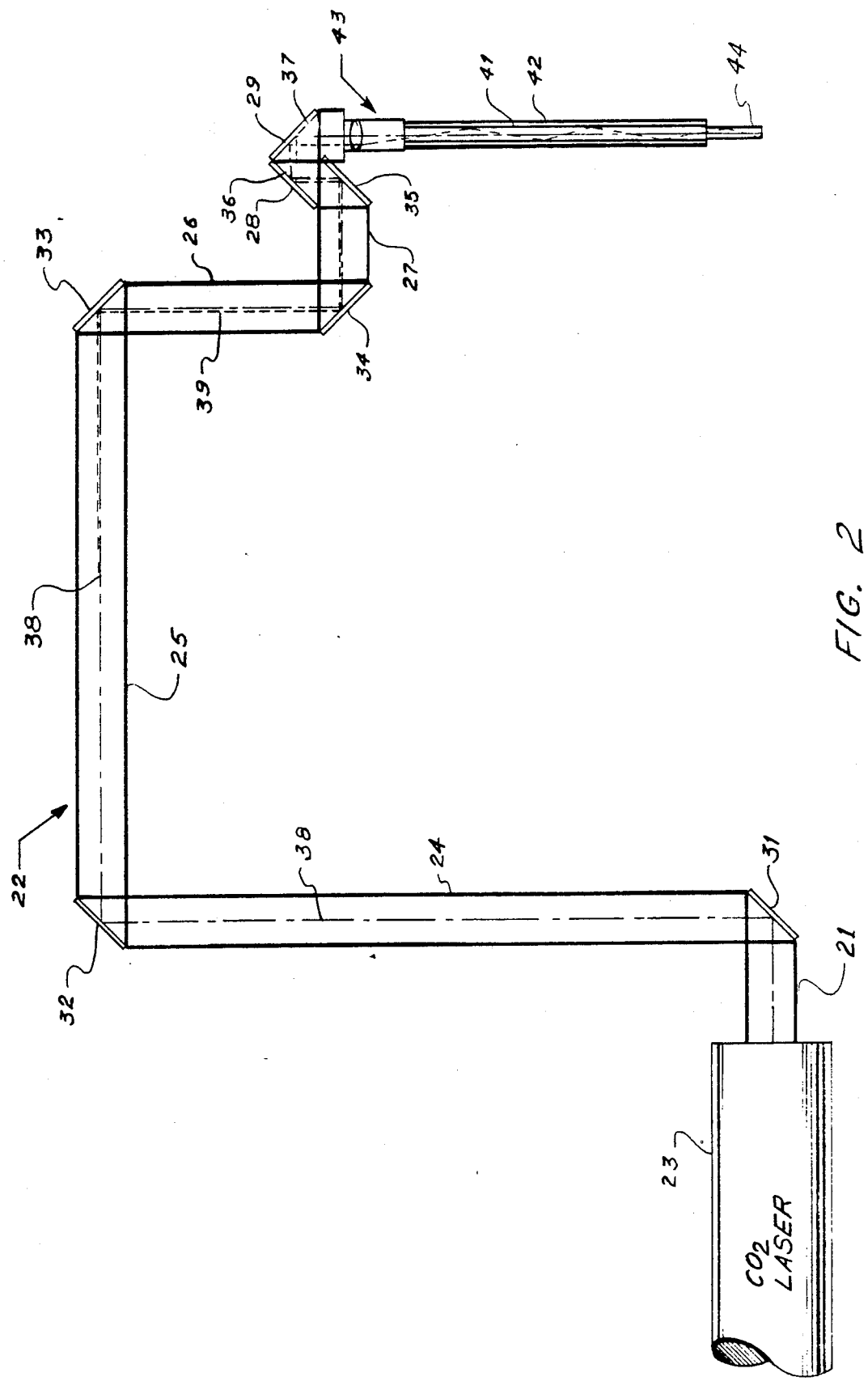
FIG. 2 is a schematic illustration of a preferred embodiment of the instant invention.

FIG. 2 is a schematic representation of a preferred embodiment of the invention. It is particularly designed for delivering $CO_2$ (carbon dioxide) laser radiation to an operating site. An entry end 21 of an articulated arm, referred to generally by the reference numeral 22, is connected to the head of a $CO_2$ laser 23 to receive the output radiation thereof. The arm 22 comprises numerous articulation sections represented by the reference numerals 24-29 (the entry end 21 is also such a section).

Corner reflectors 31-37 at the joints between each of the sections angularly change the path of the laser radiation as necessary to follow the articulations. The desired center of this path is represented by arm section center line 38. While in general the radiation optic axis coincides with the center lines of the articulated arm sections, because of angular errors and path length differences introduced by the articulations, the radiation path optic axis deviates slightly from the arm section center lines. The former is represented by the dotted line 39.

Deviations between radiation optic axis 39 and the center line of the arm sections depends largely on the nature of the articulations through which the radiation passes. Moreover, constant deviations are sometimes present due to misalignments.

The delivery arrangement of the preferred arrangement of the invention further includes an optical waveguide in the form of a tubular, hollow air core waveguide 41. (As mentioned previously, an optical waveguide typically will only accept or "couple" radiation at its entry end meeting certain criteria.) Waveguide 41 is located within an endoscope 42 designed to facilitate entry of the delivery arrangement into a body cavity for a desired operation.

Moreover, the waveguide includes a removable tip section 44 which can be replaced when desired. In this connection, it is this tip which is at an operating site and in use may become clogged or contaminated. Replacement of the tip restores the $CO_2$ laser radiation delivery arrangement to its original transmission properties.

It has been found that a hollow air core waveguide of ceramic alumina ($Al_2O_3$) works excellently in the combination of the invention. While such waveguide itself is not flexible, it provides the precision of delivery that is desirable. The articulated arm of the combination provides the flexibility.

A hollow air core waveguide which itself is flexible can be used to add flexibility to that imparted by the arm 22. A hollow air core sapphire (monocrystalline $Al_2O_3$) tube can be used for this purpose. Such a flexible waveguide provides desired flexibility at the body cavity. In this connection, the endoscope 42 can be selected to be flexible to accommodate the waveguide itself, or even can be eliminated if the waveguide does not need protection or itself includes protective sheathing or the like. Use of sapphire tubing has the added advantage of efficient guiding through the tubing itself of illuminating radiation, such as radiation from a HeNe laser light source as discussed below.

Other materials also can be used for hollow, air core waveguides. For example, silicon carbide (SiC), germanium oxide (GeO$_2$), aluminum nitride (AlN), silicon nitride (SiN) or beryllium oxide (BeO) could be used. Moreover, the waveguide structure could be a composite of an outer tube, such as one of quartz (SiO$_2$) on the interior surface of which a thin layer of a material such as aluminum oxide, is deposited via, for example, chemical vapor deposition (CVD). The important point is that the cladding material that will interact with the radiation has an index of refraction (n) which is smaller than 1, the index of refraction of the air core, at the principle CO$_2$ laser wavelength of 10.6 microns. The paper identified earlier by one of the inventors describes various IR fiber materials that can be used for a fiberoptic waveguide in the combination of the invention.

The tip section 44 does not necessarily have to be of the same material as the main section of the waveguide. For example, when the waveguide is a ceramic alumina tube as discussed above, the tip can be sapphire tubing to provide flexibility right at the operating site.

An optical coupler, generally referred to by the reference numeral 43, is positioned between the arm 22 and the entry end of the optical waveguide to condition radiation emanating from the arm for receipt at the entry end of the waveguide. If the coupler does not direct the laser light onto the waveguide with a small coupling loss, the entry end of the waveguide could be damaged by the high power laser radiation. When the delivery arrangement is designed for delivering radiation having a frequency of 10.6 microns from a CO$_2$ laser to the entry end of a hollow air core guide, it is desirable that the coupler 43 be constructed to focus such radiation received from the arm to deviate angularly no more than about ± five milliradians (mrad) from a center line extending between the arm output end and the optical waveguide entry end. If the optical waveguide is a fiberoptic waveguide having infrared fibers, it is desirable that the coupler be constructed to focus 10.6 micron radiation so that it will not deviate angularly more than about ± ten mrad from such center line. The coupler also is preferably constructed to direct CO$_2$ radiation to the entry end of the waveguide that deviates transversely from the center line by no more than about ±two millimeters (mm).

Figure 3:
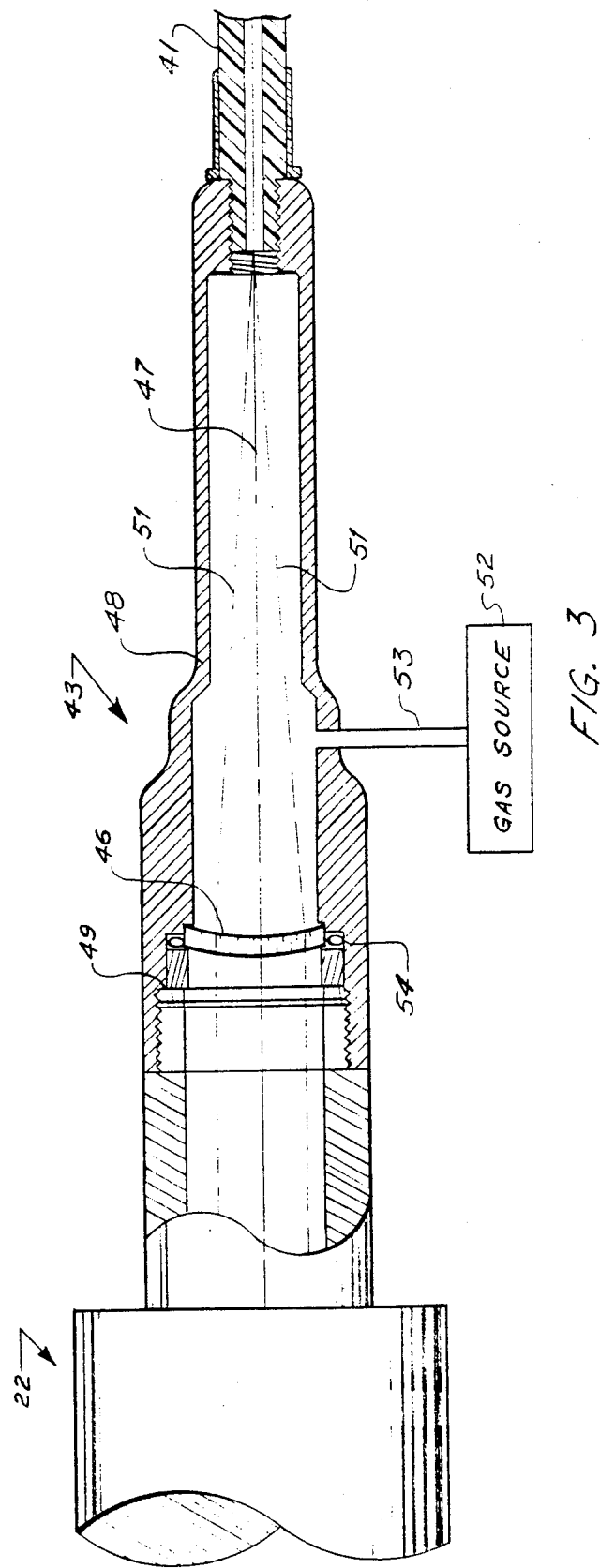
FIG. 3 is an enlarged sectional and diagrammatic view of the delivery arrangement of FIG. 2, showing constructional details of a preferred coupler arrangement.

Articulated arms themselves can be responsible for imprecision in beam delivery. There are variations from arm to arm, introduced during the manufacturing and product shipment process. Moreover, individual arms vary over a period of time primarily due to misuse in the field. Thus, the coupler of the invention most desirably is designed to compensate for such arm variations, in addition to merely acting to couple radiation from an arm to an optical waveguide. To this end, a preferred embodiment of the coupler 43 includes a focusing lens 46 (FIG. 3) designed to accomplish these results. Lens 46 is positioned on the coupler center line 47 to receive radiation from the output end of the articulated arm 22 and focus the same at the entry end of the optical waveguide. That is, the lens 46 is retained in position in a housing 48 by a pressure ring and retaining ring combination 49. In a particular arrangement which has been constructed, lens 46 was an anti-reflection coated, zinc selenide lens having an output focal length of sixty-three and one-half millimeters. The path of radiation is represented in FIG. 3 by dotted ray lines 51.

It is desirable when the invention is used at a site interiorly of a body, to prevent debris, fluid, etc at such site from interfering with the effectiveness of the treatment. Means are schematically illustrated in FIG. 3 as part of the coupler, for purging a hollow waveguide. That is, a gas source 52, such as a source of carbon dioxide, is connected to the coupler via a schematically illustrated conventional tubing and coupling arrangement 53 between the lens 46 and the entry end of the waveguide. The housing is hermetically sealed at the lens 46 by, for example, an O-ring 54 so that gas provided by the source 52 will be forced to flow through the hollow waveguide and thus purge the same. While the purge gas could be provided as a continual flow at a minimal flow rate, i.e., between 0.1 and 3 liters per minute, it will be recognized by those skilled in the art that in some situations pulses of purge gas at higher flow rates also can be used. It has been found that a continuous flow rate of between 0.2 and 0.5 liters per minute is sufficient to prevent debris from entering a waveguide in gynecology surgery, yet is not so high that tissue is blown and distorted.

It should be noted that with this arrangement the coupler can be sterilized and sterile gas used as the purge gas. The gas source may come from a separate supply or come from the assist gas normally used with medical CO$_2$ laser systems.

It is desirable in most instances to provide illuminating radiation at a surgical site. Such illuminating radiation (or light) is often delivered to the operating site by the same delivery arrangement used to deliver the operating radiation. In this connection, a HeNe laser is often provided in a CO$_2$ laser head for delivering coaxially with the CO$_2$ beam, a HeNe beam for illumination.

Figure 4:
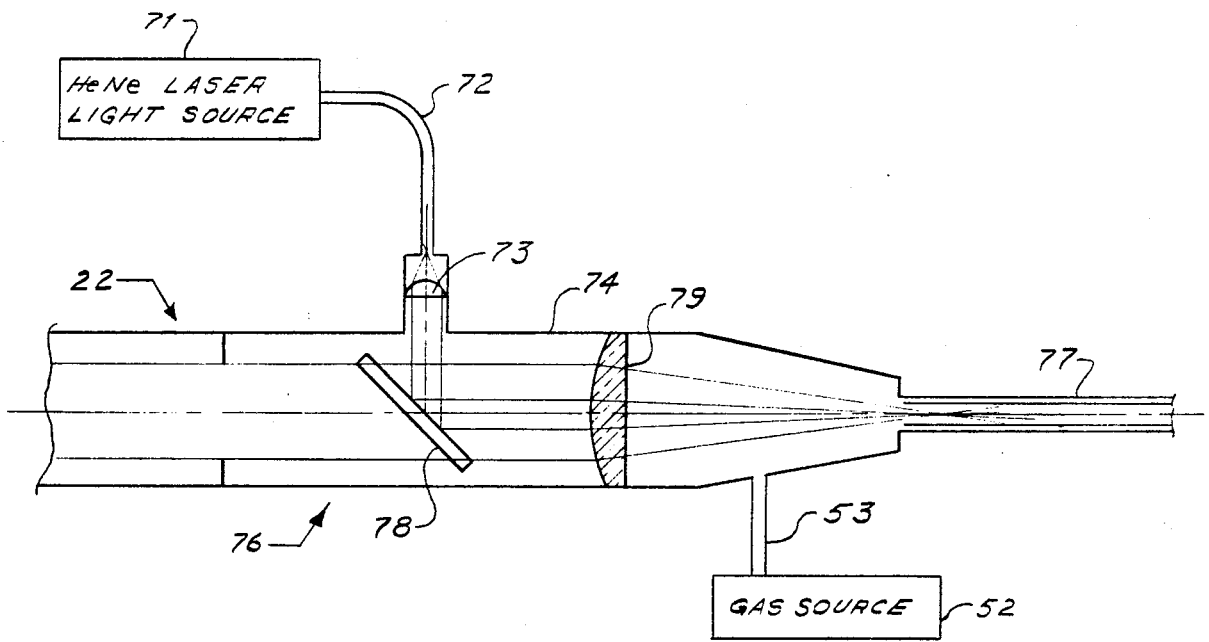
FIG. 4 is a schematic showing of an alternate coupler arrangement particularly designed to minimize the misalignment problems an articulated arm can introduce to an illuminating beam.

FIG. 4 illustrates a preferred arrangement of the instant invention for boosting the illumination. The misalignment typically caused by an articulated arm also will affect the visible radiation. The coupler of FIG. 4 receives boosting illuminating radiation directly and, thus, compensates for any loss to illumination radiation caused by the articulated arm. A HeNe laser is schematically illustrated at 71 as a light source. Its output is directed by a fiberoptic waveguide 72 to an output lens 73 positioned in the sidewall 74 of the housing of the illustrated coupler 76. Lens 73 conditions the light output of the waveguide 72 as desired to provide parallel rays of radiation to lens 79 for focusing into the waveguide portion of the delivery arrangement. While such waveguide portion is illustrated as a tubular air core waveguide 77, it could be a fiberoptic waveguide. A beam splitter 78 is positioned in the path of the radiation emanating from the lens 73 to reflect the same through the coupler lens 79 for focusing at the entry end of the waveguide. Such beam splitter is designed to allow efficient transmission therethrough of treatment radiation so the latter also will be received by the lens 79 and focused to the entry end of the waveguide.

It will be seen that with such construction, the boosting illuminating radiation is introduced into the delivery arrangement at a location at which the articulations provided by the articulated arm do not interfere with the precise positioning of the illuminating spot. The advantage of this "bypassing," rather than merely relying on the coupler to provide correction of the original illuminating radiation just as it does the surgical radiation, is that the affect of the arm on the intensity of the final illuminating light is reduced.

It should be noted that this embodiment also includes a gas purging arrangement made up of a gas source 52 and a conduit 53.

While the invention has been described in connection with preferred embodiments thereof, it will be appreciated by those skilled in the art that many modifications and variations can be made without departing from its spirit. For example, although with all arrangements except for that shown in FIG. 6 the exit end of the articulated arm is collinear with the entry end of the waveguide, this is not necessary. That is, the coupler (or other structure) can include reflectors or the like to change the path of the surgical radiation. In this connection, the reference in the specification and in the claims to a "center line" extending between the arm exit end and the waveguide entry end may be line which follows reflectors or otherwise angled between the arm and waveguide to follow the desired path of the radiation which is conditioned by the coupler. It is therefore intended that the coverage afforded applicant be limited only by the claims and equivalents.

What is claimed is:

1. A laser radiation delivery arrangement for a laser medical system comprising, in combination:
   A. An articulated arm coupled to a laser to receive radiation generated thereby and direct the same via articulations to an output end thereof;
   B. A hollow, air core optical waveguide probe to receive laser radiation from said output end of said arm and guide the same from an entry end thereof to an exit end, the cladding material of said waveguide probe having an index of refraction which is smaller than one and being aluminum oxide; and
   C. An optical coupler positioned to receive laser radiation emanating from the output end of said articulated arm and condition the same for receipt at the entry end of said optical waveguide probe.

2. The laser radiation delivery arrangement of claim 1 in which said laser to which said articulated arm is coupled is a $CO_2$ laser and the principle component of radiation generated thereby and coupled into said articulated arm has a wavelength of 10.6 microns.

3. The laser radiation delivery arrangement of claim 2 wherein said coupler is positioned and constructed to condition radiation received from the arm output end of receipt by said waveguide entry end that deviates angularly from a center line extending between said arm output end and said waveguide entry end, by as much as ±5 millliradians and deviates transversely from such center line by as much as ±2 millimeters.

4. The laser radiation delivery arrangement of claim 2 wherein said coupler includes a focusing lens for receiving radiation from said output end of said articulated arm and focusing the same to said entry end of said optical waveguide.

5. The laser radiation delivery arrangement of claim 4 further including means separate from said articulated arm for delivering illuminating radiation to said coupler for conditioning to be received at said entry end of said guide within the numerical aperture thereof.

6. The laser radiation delivery arrangement of claim 1 further including means for delivering a purge gas to said coupler for flow through said hollow waveguide.

7. The laser radiation delivery arrangement of claim 1 wherein said optical waveguide has two sections, a main body section to receive laser radiation from said output end of said articulated are, and a replaceable tip section for receiving said radiation from said main body section and guiding the same to adjacent to a desired site on mammalian tissue.

8. The laser radiation delivery arrangement of claim 1 wherein said hollow waveguide is a ceramic alumina tube.

9. The laser radiation delivery arrangement of claim 1 wherein said hollow waveguide is a sapphire tube.

* * * * *